(12) United States Patent
Stetzer

(10) Patent No.: US 8,445,044 B2
(45) Date of Patent: May 21, 2013

(54) FOOD THICKENING AGENT, METHOD FOR PRODUCING FOOD THICKENING AGENT

(75) Inventor: Douglas A. Stetzer, Superior, WI (US)

(73) Assignee: Kent Precision Foods Group, Inc., Muscatine, IA (US)

( * ) Notice: Subject to any disclaimer, the term of this patent is extended or adjusted under 35 U.S.C. 154(b) by 392 days.

(21) Appl. No.: 12/596,217

(22) PCT Filed: May 6, 2008

(86) PCT No.: PCT/US2008/005905
§ 371 (c)(1),
(2), (4) Date: Oct. 16, 2009

(87) PCT Pub. No.: WO2008/137181
PCT Pub. Date: Nov. 13, 2008

(65) Prior Publication Data
US 2010/0178397 A1    Jul. 15, 2010

Related U.S. Application Data

(60) Provisional application No. 60/928,014, filed on May 7, 2007.

(51) Int. Cl.
*A23B 7/157* (2006.01)
*A23L 1/05* (2006.01)

(52) U.S. Cl.
USPC .......................................... 426/267; 426/573

(58) Field of Classification Search
USPC ....................................................... 426/267
See application file for complete search history.

(56) References Cited

U.S. PATENT DOCUMENTS

| | | | |
|---|---|---|---|
| 2,440,365 A | 4/1948 | Copping et al. |
| 3,201,317 A | 8/1965 | Miller |
| 3,750,908 A | 8/1973 | Bauerlein et al. |
| 3,773,752 A | 11/1973 | Buchanan et al. |
| 3,949,104 A | 4/1976 | Cheng et al. |
| 4,107,343 A | 8/1978 | Petricca |
| 4,132,793 A | 1/1979 | Haber et al. |

(Continued)

FOREIGN PATENT DOCUMENTS

| CA | 2254560 A1 | 9/1999 |
|---|---|---|
| CA | 2574247 A1 | 7/2007 |

(Continued)

OTHER PUBLICATIONS

Buckley, John E. et al., "Feeding Patients with Dysphagia." Nursing Forum. vol. XV, No. 1 (1976), pp. 69-85.

(Continued)

*Primary Examiner* — D Lawrence Tarazano
*Assistant Examiner* — Katherine Deguire
(74) *Attorney, Agent, or Firm* — Fitch Even Tabin & Flannery LLP

(57) ABSTRACT

The invention provides a food and water thickener and a method for preparing the food and water thickener. The food thickener comprises pretreated mineral water, xanthan, food preservative, a first antimicrobial and chelating agent, and a sequestering agent, wherein the food thickener has a density of between 750 and 1250 grams per liter. The method for producing the thickener incorporates pretreatment of mineral water and xanthan, and specific heating steps. Also provided is method for producing thickened alcoholic beverages. The invention further provides a method for invoking a swallow response in dysphagic patients, the method comprising increasing the mass of food to between 750 mg per liter and 1500 mg per liter; and orally administering the food to dysphagic patients.

32 Claims, 1 Drawing Sheet

U.S. PATENT DOCUMENTS

| | | |
|---|---|---|
| 4,135,979 A | 1/1979 | Corley et al. |
| 4,229,825 A | 10/1980 | Guidoux |
| 4,236,820 A | 12/1980 | Walker |
| 4,252,835 A | 2/1981 | Maerker et al. |
| 4,269,974 A | 5/1981 | Wintersdorff |
| 4,299,825 A | 11/1981 | Lee |
| 4,427,681 A | 1/1984 | Munshi |
| 4,430,349 A | 2/1984 | Malone et al. |
| 4,503,084 A | 3/1985 | Baird et al. |
| 4,563,366 A | 1/1986 | Baird et al. |
| 4,620,932 A | 11/1986 | Howery |
| 4,654,086 A | 3/1987 | Baird et al. |
| 4,670,550 A | 6/1987 | Bleeker et al. |
| 4,671,966 A | 6/1987 | Giddey et al. |
| 4,689,219 A | 8/1987 | Sugden |
| 4,774,093 A | 9/1988 | Provonchee et al. |
| 4,828,724 A | 5/1989 | Davidson |
| 4,846,934 A | 7/1989 | Carberry |
| 4,855,156 A | 8/1989 | Singer et al. |
| 4,859,484 A | 8/1989 | Bielskis et al. |
| 4,894,335 A | 1/1990 | Peignier et al. |
| 4,996,070 A | 2/1991 | Nafisi-Movaghar |
| 4,997,571 A | 3/1991 | Roensch et al. |
| 5,165,946 A | 11/1992 | Taylor et al. |
| 5,202,146 A | 4/1993 | Singer et al. |
| 5,251,699 A | 10/1993 | Lau et al. |
| 5,270,459 A | 12/1993 | Shatzman et al. |
| 5,300,302 A | 4/1994 | Tachon et al. |
| 5,302,292 A | 4/1994 | Soeder et al. |
| 5,338,561 A | 8/1994 | Campbell et al. |
| 5,362,713 A | 11/1994 | Westland et al. |
| 5,385,748 A | 1/1995 | Bunger et al. |
| 5,466,464 A | 11/1995 | Masaki et al. |
| 5,536,825 A | 7/1996 | Yeh et al. |
| 5,607,714 A | 3/1997 | Connolly |
| 5,633,028 A | 5/1997 | Wong |
| 5,641,532 A | 6/1997 | Pflaumer et al. |
| 5,648,093 A | 7/1997 | Gole et al. |
| 5,654,027 A | 8/1997 | Chalupa |
| 5,811,148 A | 9/1998 | Chiu et al. |
| 5,837,272 A | 11/1998 | Fierro, Jr. et al. |
| 5,869,029 A | 2/1999 | Graff-Andersen et al. |
| 5,869,118 A | 2/1999 | Morris et al. |
| 5,932,235 A | 8/1999 | Ninomiya et al. |
| 5,976,084 A | 11/1999 | Tymchuck |
| 5,997,907 A | 12/1999 | Goswami et al. |
| 6,001,408 A | 12/1999 | Dudacek et al. |
| 6,007,848 A | 12/1999 | Hendrick et al. |
| 6,022,576 A | 2/2000 | Cirigliano et al. |
| 6,033,712 A | 3/2000 | Greenshields et al. |
| 6,033,713 A | 3/2000 | Sheldon |
| 6,036,982 A | 3/2000 | Lehmberg et al. |
| 6,036,986 A | 3/2000 | Cirigliano et al. |
| 6,056,984 A | 5/2000 | Ekanayake et al. |
| 6,077,501 A | 6/2000 | Sickora et al. |
| 6,139,895 A | 10/2000 | Zablocki et al. |
| 6,149,962 A | 11/2000 | Loh et al. |
| 6,162,471 A | 12/2000 | Sheldon |
| 6,174,549 B1 | 1/2001 | Greenshields et al. |
| 6,200,623 B1 | 3/2001 | Dudacek et al. |
| 6,214,406 B1 | 4/2001 | Reimerdes |
| 6,277,395 B1 | 8/2001 | Fukui et al. |
| 6,303,039 B1 | 10/2001 | Back et al. |
| 6,326,040 B1 | 12/2001 | Kearney et al. |
| 6,423,348 B1 | 7/2002 | Mickus |
| 6,455,090 B1 | 9/2002 | Uzuhashi et al. |
| 6,458,395 B1 | 10/2002 | Emoto |
| 6,461,589 B1 | 10/2002 | Robbins |
| 6,559,187 B2 | 5/2003 | Chandran et al. |
| 6,613,400 B1 | 9/2003 | Murphy et al. |
| 6,686,341 B1 | 2/2004 | Bijlsma et al. |
| 6,693,216 B2 | 2/2004 | Raczek et al. |
| 7,052,725 B2 | 5/2006 | Chang et al. |
| RE39,125 E | 6/2006 | Fukui et al. |
| 7,288,277 B2 | 10/2007 | Zhao et al. |
| 7,320,810 B2 | 1/2008 | Wuersch et al. |
| 7,429,326 B2 | 9/2008 | Levy |
| 7,638,150 B2 | 12/2009 | Holahan |
| 7,764,992 B2 | 7/2010 | Mabary et al. |
| 2001/0036439 A1 | 11/2001 | Robbins |
| 2003/0044351 A1 | 3/2003 | Robbins |
| 2004/0197456 A1 | 10/2004 | Holahan |
| 2004/0228954 A1 | 11/2004 | Tejayadi |
| 2004/0258823 A1 | 12/2004 | Dufresne et al. |
| 2006/0051296 A1 | 3/2006 | Holahan |
| 2006/0207925 A1 | 9/2006 | Levy |
| 2007/0138093 A1 | 6/2007 | Bossler et al. |
| 2007/0172568 A1 | 7/2007 | Spelman |
| 2007/0196495 A1 | 8/2007 | Soltero |
| 2007/0224126 A1 | 9/2007 | Dufresne et al. |
| 2007/0264401 A1 | 11/2007 | Taormina et al. |
| 2008/0223799 A1 | 9/2008 | Tsai |
| 2008/0226800 A1 | 9/2008 | Lee et al. |
| 2008/0248184 A1 | 10/2008 | Esteve et al. |
| 2009/0074940 A1 | 3/2009 | Sliwinski |
| 2009/0162515 A1 | 6/2009 | Dufresne et al. |
| 2009/0291192 A1 | 11/2009 | Holahan |
| 2010/0055207 A1 | 3/2010 | Holahan |
| 2010/0055262 A1 | 3/2010 | Holahan |
| 2010/0119559 A1 | 5/2010 | Dansereau et al. |
| 2010/0166917 A1 | 7/2010 | Smith |
| 2010/0178397 A1 | 7/2010 | Stetzer |
| 2010/0215804 A1 | 8/2010 | Goto et al. |
| 2010/0233320 A1 | 9/2010 | Sunvold et al. |
| 2011/0135568 A1 | 6/2011 | Holahan |
| 2011/0135799 A1 | 6/2011 | Holahan |

FOREIGN PATENT DOCUMENTS

| | | |
|---|---|---|
| DE | 19918210 A1 | 2/2000 |
| DE | 19918210 A1 | 11/2010 |
| EP | 0130771 | 1/1987 |
| EP | 0620012 A1 | 10/1994 |
| EP | 0620112 A1 | 10/1994 |
| EP | 1046347 A1 | 10/2000 |
| EP | 1078981 A1 | 2/2001 |
| EP | 1810579 A1 | 7/2007 |
| JP | 06040950 A | 2/1994 |
| JP | 07274915 A | 10/1995 |
| JP | 11124342 | 5/1999 |
| JP | 1187827 | 7/1999 |
| JP | 11187827 | 7/1999 |
| JP | 10131478 | 11/1999 |
| JP | 10229517 | 11/1999 |
| JP | 11318356 | 11/1999 |
| JP | P200041594 | 2/2000 |
| JP | 2000135070 A | 5/2000 |
| JP | 2000325041 A | 11/2000 |
| WO | 9934690 | 8/1998 |
| WO | 9925208 | 5/1999 |
| WO | 9925208 A1 | 5/1999 |
| WO | 0057727 A1 | 10/2000 |
| WO | 9934690 | 10/2000 |
| WO | 0115743 A2 | 3/2001 |
| WO | 0179521 A1 | 10/2001 |
| WO | 0211716 A2 | 2/2002 |
| WO | 03011051 A1 | 2/2003 |
| WO | 2004069179 | 8/2004 |
| WO | 2006054886 | 5/2006 |
| WO | 2008137181 | 11/2008 |

OTHER PUBLICATIONS

Li, Meijing et al., "Viscosity Measurements of Barium Sulfate Mixtures for Use in Motility Studies of the Pharynx and Esophagus." Dysphagia 7 (1992), pp. 17-30.

Siddall, Pauline M et al., "Dysphagia in the elderly: a learning experience for those new to this field." Caring to Communicate. International Journal of Language and Communication Disorders, vol. 30, Issue S1 (Oct. 1995), pp. 423-432.

Winstein, Carolee J., "Neurogenic Dysphagia: Frequency, Progression, and Outcome in Adults Following Head Injury." Physical Therapy. vol. 63, No. 12 (Dec. 1983), pp. 1992-1997.

Written Opinion of the International Searching Authority, PCT application No. PCT/US2008/005905, Aug. 6, 2008, 4 pp.

Sopade, et al., Eur. Food Res Technol 224:555-560.

Sopade et al., Moisture absorption characteristics of food thickeners used for the management of swallowing dysfunctions, Eur. Food Res. Technol., 2007, 555-560, 224, Springer Verlag, United States.

European Patent Office, European Search Report, Mar. 9, 2011, pp. 1-57.

Dysphagia 9:209-217; "Epidemiology and Dysphagia"; Keith V. Kuhlemeier, PhD, MPH; 1994; p. 209-217 (9 pages total).

American Speech-Language Hearing Association; "Communication Facts, Special Populations: Dysphagia"; 2001 Edition; http://orofessional.asha.ora/research/dvsohaaia.htm (6 pages total).

Journal of Neuroscience Nursing, Apr. 1989, vol. 21, No. 2; "Dysphagia in Huntington's Disease"; Vicki P. Hunt, RN, Francis O. Walker, MD; p. 92-95 (4 pages total).

Abstract; Research Disclosure, XP—002305761; "Concentrated Gellan Gum Gel (5%) Suitable to Gel Various Other Systems"; King, A.H.; 1996 (1 page total).

Arch Neurol—vol. 42, Jan. 1985; "Dysphagia in Huntington's Disease"; Norman A. Leopold, DO, Marion C. Kagel, MA; p. 57-60 (4 pages total).

Ikegami, S. et al., "Effect of viscous indigestible polysacchardes on pancreatic-billary secretion and digestive organs in rats", Journal of Nutrition, 120, pp. 353-360, 1990.

Dietary Fiber Definition Committee, "The definition of dietary fibre", Cereal Foods World, 46, pp. 112-126, Mar. 2001.

Jenkins, D.JA et al., "Dietary fibres, fibre analogues, and glucose tolerance: importance of viscosity", British Medical Journal, 1, pp. 1392-1394, May 27, 1978.

Torsdottir, I. et al., "A small dose of soluble alginate-fiber affects postprandial glycemia and gastric emptying in humans with diabetes", Journal of Nutrition, 121, pp. 795-799, 1991.

Jenkins; D.JA et al., "Unabsorbable carbohydrates and diabetes: decreased post-prandial hyperalycaemia", The Lancet, 308, pp. 172-174, Jul. 24, 1976.

Wolever, T.M.S. et al., "Guar gum and reduction of post-prandial glycaemia: effect of incorporation into solid food, liquid food, and both", British Journal of Nutrition, 41, pp. 505-510, 1979.

Reppas, C. et al., "High viscosity hydroxypropylmethylcellulose reduces postprandial blood glucose concentrations in NIDDM patients", Diabetes Research and Clinical Practice, 22, pp. 61-69, 1993.

Canadian Examiner's Notice of Allowance on patent application No. 2509715 dated Oct. 26, 2009 (1 pg.).

American Speech-Language Hearing Association; "Special Populations: Stroke"; 2002 Edition; http://professional.asha. org/research/dysphagia.htm (6 pgs.).

Applied microbiology and biotechnology, Aug. 1998, vol. 50, No. 2, "Xanthan gum biosynthesis and application:a biochemical/genetic perspective", A. Becker a F. Katzen a A. PuE hler a L. lelpi, p. 145-152 (8 pgs.).

Art. 96(2) EPC Communication, European Application No. 027596246.8, Date of Mailing Apr. 10, 2007, (5 pgs.).

Art. 96(2) EPC Communication, European Application No. 027596246.8, Date of Mailing Nov. 13, 2007, (3 pgs.).

Art. 94(3) EPC Communication, European Application No. 027596246.8, Date of Mailing Apr. 16, 2008, (6 pgs.).

Art. 94(3) EPC Communication, European Application No. 027596246.8, Date of Mailing Nov. 13, 2008, (3 pgs.).

Art. 96(2) EPC Communication, European Application No. 04707165.9, Date of Mailing Aug. 7, 2006, (5 pgs.).

Art. 94(3) EPC Communication, European Application No. 04707165.9, Date of Mailing Apr. 7, 2008, (5 pgs.).

Australian Examiner's report No. 5 on patent application No. 2002324592 dated Apr. 30, 2008 (3 pgs.).

Australian Examiner's report No. 6 on patent application No. 2002324592 dated Jun. 5, 2008 (3 pgs.).

Canadian Examiner's Notice of Allowance on patent application No. 2459924 dated Feb. 23, 2009 (1 pg.).

Canadian Examiner's Requisition on patent application No. 2459924 dated Jul. 21, 2005 (4 pgs.).

Canadian Examiner's Requisition on patent application No. 2459924 dated Apr. 3, 2006 (4 pgs).

Canadian Examiner's Requisition on patent application No. 2459924 dated Nov. 29, 2006 (4 pgs.).

Canadian Examiner's Requisition on patent application No. 2459924 dated Sep. 7, 2007 (3 pgs.).

Canadian Examiner's Requisition on patent application No. 2459924 dated Apr. 22, 2008 (5 pgs.).

Canadian Examiner's requisition on patent application No. 2509715 dated Feb. 19, 2009 (3 pgs.).

Compiled by a Castrogiovanni, Communication Facts: Special Populations: Dysphagis BO 2002 Edition, ASHA Resource Center, htlp:IIprofessional.asha.orglresearchldysphagia.html (3 pgs.).

Decision to Grant EPC Communication, European Application No. 04707165.9, Date of Mailing Dec. 30, 2008, (2 pgs.).

European Search Report, European Application No. 027596246.8, Date of Mailing Aug. 12, 2004, (4 pgs.).

European Search Report, European Application No. 04707165.9, Date of Mailing Jan. 27, 2006, (4 pgs.).

European Search Report, European Application No. 09005203.6, Date of Mailing Aug. 12, 2004, (6 pgs.).

Intent to Grant EPC Communication, European Application No. 04707165.9, Date of Mailing Apr. 27, 2009, (32 pgs.).

Intent to Grant EPC Communication, European Application No. 04707165.9, Date of Mailing Jul. 28, 2008, (33 pgs.).

PCT Notifcaton of Tansmital of Intenational Preliminary Examination Report, International Applicaion No. PCT! US02/24525, Date of Mailing Aug. 23, 2004; (5 pgs.).

PCT Notifcation of Transmital of the Intenational Search Report or the Declaraton International Applicaton No. PCT|US02/24525, Date of Mailing Dec. 2, 2002; (6 pgs.).

Written Opinion of the International Searching Authority, International Application No. PCT|US02/24525, Date of Mailing Feb. 18, 2004; (5 pgs.).

Xanthan gum, G. Sworn, Monsanto (Kelco Biopolymers, Tadworth), in Handbook of Hydrocolloids, ed. G.O. Phillips and P. Williams, Woodhead Publishing Ltd, Cambridge, England, Jul. 2000, pp. 103-115. Available at: http://docencia.izt.uam.mx/epa/quim_alim/tareas/xantana.pdf.

Australian Examiner's report No. 4 on patent application No. 2002324592 dated Mar. 28, 2008 (4 pgs.).

Castellanos, V. H., Phd, RD; Butler, E. RD; Gluch, L., RD; Burke; B.; RD, Use of Thickened Liquids in Skilled Nursing Facilities, Jrnl of the Amer Dietetic Association Aug. 2004.

NYEEI: Otolaryngology: Faqs About Swallowing Disorders, Online, NYEEI: http://www.nyee.edu/faqlist.html?tablename=faz&key=48&print=.

Deis, Ronald C., Ph.D., Dietary Fiber: A Healthy Discussion, Weeks Publishing Co, Jan. 1999, Design Elements Online, http://www.foodoroductdesian.com/archive/1990/0199de.html.

Edmonds, C., M.R.C.P.D.P.M., Huntington'S Cora, Dysphagia and Death, The Medical Journal of Australia, Aug. 6, 1966.

Department of Health and Human Services, FDA; 21 CFR Part 201 (DKT 90N0364 RIN0905-AD91, Regulation of Medical Foods: Advance Notice of Proposed Rulemaking Federal Redister vol. 61.

U.S. Food and Drug Administration Center for Food Safety and Applied Nutrition [Online] http://www.cfsan.fda.gov/-dms/ds-medfd.html Aug. 24, 2001.

Lontong, V.; Texture and Flavor Characteristics of Beverages Containing Commercial Thickening Agents for Dysphagia Diets, Journal of Food SCience, vol. 68, Nov. 4, 2003 1537-1541.

PCT Notfcation of Transmittal of the International Seach Report or the Declaration, International Applicaton No. PCT/US02/24525, Date of Mailing Dec. 2, 2002; 6 pages.

English Translation of Published Japanese Patent Appiication No. JP11187827A (16 pgs.).

International Search Report 02759246.8-1221-US02/24525 P71214EPOO 4 pages.

Department of Health and Human Services; Food & Drug Administration; Warning Statements Required for Over-The-Counter Drugs Containing Water-Soluble Gums as Active Ingredients Federal Register; vol. 58, No. 164; Thursday, Aug. 26, 1993/Rules and Regulations (8 pages total).

American College of Radiology; ACR Appropriateness Criteria; "Imaging Recommendations for Patients with Dysphagia"; p. 225-230 (6 pages total).

American Speech-Language Hearing Association; "Communication Facts, Special Populations: Dysphagia"; 1999 Edition (3 pages total).

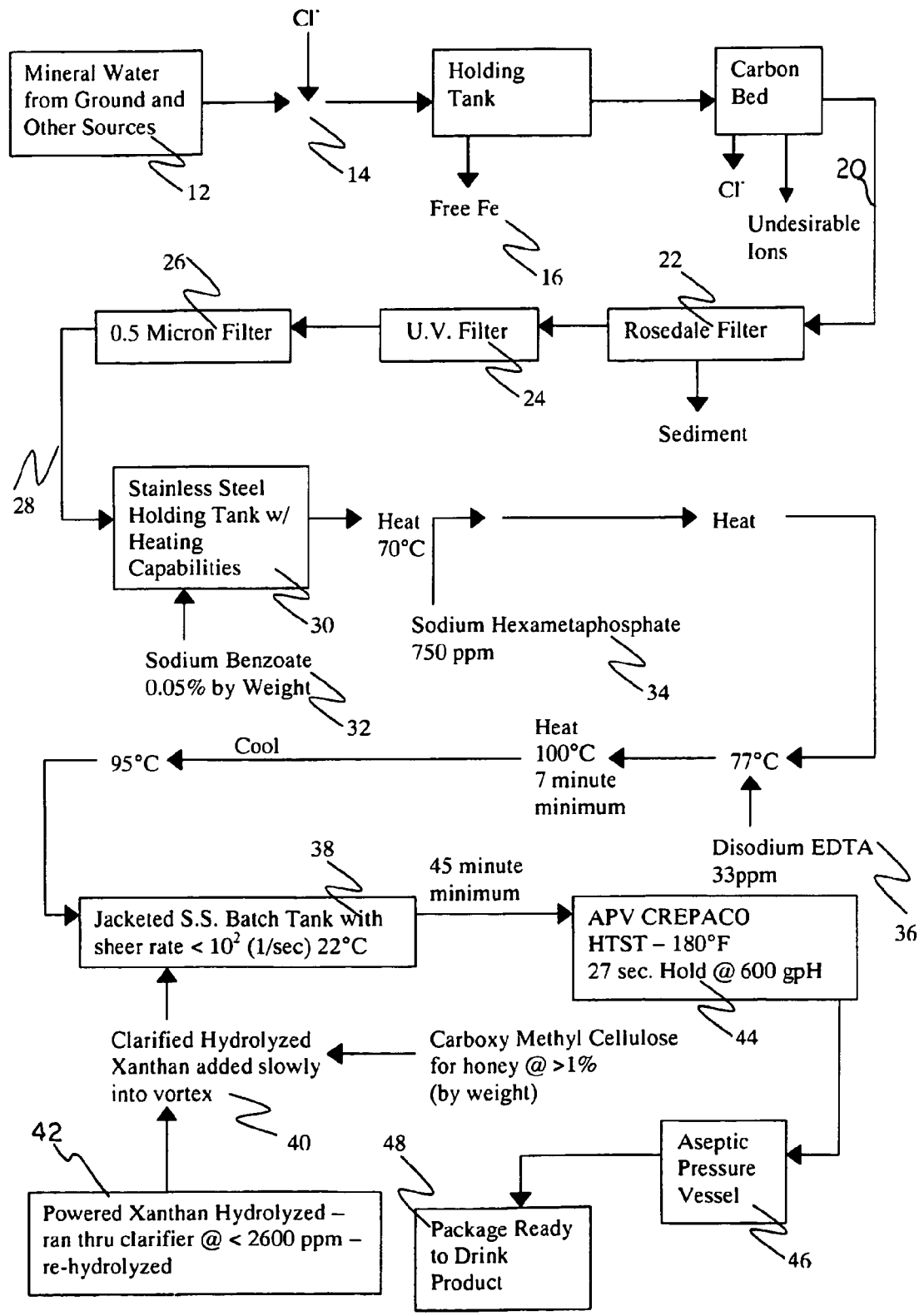

FOOD THICKENING AGENT, METHOD FOR PRODUCING FOOD THICKENING AGENT

CLAIM OF PRIORITY

This utility application claims the benefits of U.S. Provisional Application No. 60/928,014, filed on May 7, 2007.

BACKGROUND OF THE INVENTION

1. Field of the Invention

The present invention relates to a food thickening agent and a method for producing a food thickening agent, and more specifically, the present invention relates to a food thickening agent having a long shelf life for use by patients with dysphagia and a method for producing such a food thickening agent.

2. Background of the Invention

Patients with dysphagia have difficulty swallowing food and water without aspirating it. As such, these patients have difficulty swallowing liquid and soft foods. Instead, they must mix such liquid and food with thickening agents.

Currently, manufacturers use modified food starch or xanthan gum to thicken water and other beverages. These thickeners, besides thickening the beverage, carry with them their own flavors, which need to be masked. Manufacturers, including those that use xanthan, use an acid (usually citric acid, acetic acid or others) to cover the flavor. The acid also aids in stability of the product (shelf life). What the acid does though, is bring its own flavor, which is more palatable than the starch or xanthan alone. The acid also has the tendency to yellow the product. This is not noticeable with the starch based material, as it already is cloudy and slightly yellow to begin with. It is very noticeable with the xanthan products, although some of them are naturally opaque as well. As a result of the use of these acids, the product seldom has a look or taste that is natural, especially when trying to reproduce a glass of natural looking and tasting water.

Specifically, it is not uncommon for some food thickeners based on cornstarch to mask the taste and desired consistency of carrots with as little as $5 \times 10^{-5}$ weight percent of the thickener/nourishment comprised of the food thickener. A vicious cycle then develops, whereby patients take a sip of the thickened nourishment, then set it aside perhaps to consume later. The longer the liquor sets, the longer amylase (an enzyme in saliva that is transferred to the liquor) has to break down the cornstarch, thereby reducing the thickness (and therefore the usability) of the liquor.

Also, most thickening products currently available, once processed and opened for use have shelf-lives on the order of from eight hours at room temperature, to one week at refrigeration temperatures. This is due to the instability of starch in starch products and moisture content in xanthan products (see discussion below). Thickeners that show the highest $M_E$ (end moisture content) have the highest chance of spoilage when compared to thickeners that have low $M_E$, as discussed in Liang et al. Bachelor Engineering Thesis, University of Queensland, 2004.

For example, xanthan gum is utilized as the viscous fluid in the invented mixture. In these cases, water retention is highest, due to the ease in which xanthan's hydroxyl groups form hydrogen bonds with the dispersing media, as detailed in Sopade et al., *Eur. Food Res Technol* 224:555-560. Hydration or water binding capacity of food is of prime significance for food processors and handlers because sorption properties affect storage, end-use, packaging requirements and certain physical properties.

A need exists in the art for a food thickening agent that, when mixed with food, does not alter the appearance, taste and color of the food, even in thickener loadings exceeding 40 weight percent. The agent should be viable at neutral to basic pH levels. The thickening agent should be inexpensive to manufacture. Also, the thickening agent should have a shelf life of at least 90 days, and preferably greater than 150 days. Finally, the agent should allow patients with dysphasia the opportunity to hydrate from a simple glass of water.

SUMMARY OF INVENTION

An object of the present invention is to provide a food thickener, and a method for producing a food thickener, that overcomes many of the disadvantages of the prior art.

Another object of the invention is to provide a food thickener that has a long shelf life. A feature of the invention is utilization of a sulfur and mineral scavenger in the thickener. An advantage of the invention is that the scavenger would prevent promulgation of sulfur-philic bacteria in the liquor. It, along with high heat treatment, provides a means for reducing water activity, which otherwise fosters microbial growth.

Still another object of the present invention is to provide a method for producing a food thickener having a long shelf life. A feature of the invention is the addition of an agent which scavenges free ions and elemental sulfur present in liquor components. An advantage of the invention is a minimization of discoloration of the liquor over time and a minimization of taste loss over time.

Yet another object of the present invention is to provide a method for enhancing tongue sensation in stroke patients. A feature of the invention is increasing mass of nourishment by mixing the nourishment with a high mass food thickener to produce a thickened food liquor with a density of between 750 and 1200 grams per milliliter. An advantage of the invention is that the color and flavor of the nourishment is not compromised, despite the nourishment being mixed with the food thickener. Another advantage is that the increased mass and density of the nourishment invokes a swallow response such that the stroke patients swallow the nourishment instead of aspirating it.

Briefly, the invention provides a method for preparing food and liquid thickener, the method comprising pretreating mineral water; combining the pretreated mineral water with a food preservative to produce a first mixture; heating the first mixture to a first temperature and then combining the heated mixture with a chelating/antimicrobial agent to produce a second mixture; combining the second mixture with a sequestration agent to form a third mixture and then maintaining the third mixture at a second temperature; adding xanthan to the third mixture to create a fourth mixture; and homogenizing the fourth mixture.

Also provided is a method for producing thickened alcoholic beverages, the method comprising pretreating mineral water; combining the pretreated mineral water with a food preservative to produce a first mixture; heating the first mixture to a first temperature and then combining the heated mixture with a chelating/antimicrobial agent to produce a second mixture; combining the second mixture with a sequestering agent to form a third mixture and then maintaining the third mixture at a second temperature; adding viscous fluid to the third mixture to create a fourth mixture; homogenizing the fourth mixture; mixing the homogenized mixture with fluid containing ethanol.

The invention further provides a method for invoking a swallow response in dysphagic patients, the method comprising increasing the mass of food to between 750 grams per liter and 1500 grams per liter; and orally administering the food to dysphagic patients.

BRIEF DESCRIPTION OF DRAWING

The invention together with the above and other objects and advantages will be best understood from the following detailed description of the preferred embodiment of the invention shown in the accompanying drawing, wherein:

FIG. 1 is a schematic diagram of a protocol for producing food thickener, in accordance with features of the present invention.

DETAILED DESCRIPTION OF THE INVENTION

The invention provides a process for making a more natural flavored thickened liquid or solid food. A liquid food or solid food thickener is provided that would be palatable, mix well with liquid and/or solid nourishment. In its pure form (i.e., neat), the invented thickener is as clear and colorless as water. While in the past, patients with dysphasia could only hydrate themselves from a flavored fluid or a fluid with a masked flavor, the invented formulation allows such patients to hydrate from a simple glass of water.

The thickener can be used with a myriad of liquid foods, including but not limited to water, wine, beer, distilled spirits, vegetable juice, fruit juice, soft drinks, milk, and combinations thereof. The thickener is also used with all solid foods, including but not limited to meat, fish, poultry, diary products, such as cheese and yogurt, vegetables, fruits, grains, and combinations thereof. The only requirement with the mixture of the thickener with the solid food is to puree the solid food to a desired consistency. The thickener also can be used with a myriad of powdered formulations such as protein powders, flavored powders and syrups, and various condiments.

The thickener maintains its palatability and original appearance for at least 120 days after exposure to air, typically 150 days after air exposure and up to 180 days after exposure to air; even during continuous exposure to air and/or the atmosphere. The thickener is likewise resilient to exposure to enzymes found in saliva, such as amylase, for the same period of time.

The invention provides a means for maintaining the food thickener such that its color or flavor does not degrade and end up effecting the nourishment with which it combines. Specifically, mixing EDTA with xanthan and mineral water results in a liquor which has a shelf life noted supra, typically as 150 days.

In an embodiment of the invented thickening agent, weight percents of xanthan to total food thickener are between 3 grams/liter and 11 grams/liter. An exemplary xanthan weight percent is approximately 0.7 for "nectar" formulations. Weight percents of sodium hexametaphosphate are between 83 milligrams (mg)/liter and 150 mg/liter. An exemplary sodium hexametaphosphate weight percent is approximately 0.004 for nectar formulations. Weight percents of EDTA to total food thickener are between 10 mg/liter and 30 mg/liter. An exemplary EDTA weight percent to total food thickener is approximately $4.5 \times 10^{-6}$.

While a portion of this specification features the use of xanthan as a thickener, and includes empirical data regarding same, the invention is enabled by other thickeners'. For example, aside from xanthan, other thickeners are suitable, including but not limited to polysaccharides such as Carrageenan, Guar Gum, modified food starch, cellulose-containing material, including, but not limited to, carboxyl methyl cellulose. Generally, any thickener or viscous agent, such as xanthan with an inclusion rate of between 0.1 g/L and 10 g/L is suitable. The inclusion rate is the weight percent of viscous agent necessary to confer the required viscosity, mass values, and preservation characteristics of the invented food thickener. For example, the inclusion rate for xanthan is approximately 6 grams per liter for "nectar", 10 grams per liter for "honey", and 19 grams per liter for "pudding". Nectar, honey, and pudding designations are conferred by the industry as having centipoises values of between 51-350 centipoise (cp), 351-1750 cp, and more than 1750 cp respectively.

Xanthan is a preferable thickening agent in the invented liquor given its relative stability compared to certain starches. First, as a by-product of bacterial action, xanthan is relatively particulate free, thereby eliminating the graininess associated with corn starch based products.

Second, certain enzymes in the mouth, including amylase, will not degrade xanthan, but will degrade a cornstarch product.

Also, the inventor has found that its plethora of hydroxyl ions provides xanthan with superior absorption rates. This is particularly important in patients who cannot even tolerate solid foods, as xanthan will permeate meat. This means for enhanced absorption is not lost in the instant liquor, given the latter's ability to work at pH values ranging from 4 to 9.

The liquor provides a food thickening agent that, when combined with food, does not alter the pH of the food or its the viscosity or flavor, while simultaneously increasing its water content or hydration (up to 150 times its normal level). For example, carrots have a solids content of 12 percent (corresponding to a water content of 88 weight percent). When mixed with the invented food thickener at a 1:1 weight ratio, the solids content of the now thickened carrots drops to six percent, thereby doubling its water content, and without altering the flavor or texture of the carrots. This results in increasing the patient's hydration from food intake.

Surprisingly and unexpectedly, the inventors found that adding clarified xanthan allows more water to be absorbed by the food (meat, fruits, vegetables, combinations thereof). Water weight increases range from 30 percent to 150 percent without altering the food's viscosity, or texture.

Suitable Xanthan is that which meets the specifications of the National Formulary, the Food Chemicals Codex and the J.E.C.F.A. These specifications include the following:

General Characteristics:
 Viscosity (1.0% in 1.0% KCl) 1400-1800 cP
 Particle Size 98% minimum through USS 16 mesh, 1190μ
 12% maximum through USS 80 mesh, 177μ
 Powder Color Not less than 60
 pH (1.0% Solution) 5.5 to 8.1
Standard Specifications:
 Identification Meets NF/FCC tests
 Assay Meets NF/FCC tests
 Loss on Drying Not more than 15%
 Viscosity Meets NF/FCC tests
 Ash Between 6.5% and 16%
 Arsenic Not more than 3 ppm
 Lead Not more than 5 ppm
 Heavy Metals (as Pb) Not more than 20 ppm
 Isopropyl Alcohol Not more than 750 ppm
 Pyruvic Acid Not less than 1.5%
 Nitrogen Not more than 1.5%
Microbiological:
 Total Plate Count Not more than 2000/g
 Yeast and Molds Not more than 100/g
 *Salmonella* Meets NF test
 *Escherichia coli* Meets NF test.

Shelf Life:

36 months from the certificate of analysis test date

While the xanthan starts off clear, over time it yellows. For example, when the xanthan is mixed with distilled water, or, in a separate trial, mixed with tap water, over time (usually within 30 days) the product yellowed and developed a foul taste. Specifically, the inventor found that "tap water" which contains typical elements (iron, chlorine, etc) is contraindicated with the invented process. Specifically, water gleaned from municipal water sources contains chlorine which facilitates rapid yellowing of water. This is because chlorine binds to xanthan sugars which cause an increase in opacity and yellowing.

In a third trial, the xanthan was mixed with artesian mineral water. The taste improved at the onset, however, it too yellowed and got even more distasteful over time.

EDTA was then added to aid in flavor preservation. Immediately, flavor improved. Color at first got worse. Generally, acids such as citric, acetic and ascorbic are used to mask unpalatable flavor of aging thickeners.

Prior to the mixing of Xanthan to any food preservation agents or chelating agents, sodium benzoate, potassium sorbate, citric acid, and combinations thereof is added to the mineral water to eradicate, minimize or otherwise neutralize any microbes present in the mineral water. It is important that this first antimicrobial agent be added early in the protocol. (Sodium hexametaphosphate is added later as a second antimicrobial agent.) Adding the benzoate too close to the food preservation agents and chelating agents such as acidic sodium hexametaphosphate and EDTA will cause the benzoate to become neutralized.

Next, the liquor is heated to 70 C so as to eliminate all but the most heat-resistant bacteria, or thermoduric bacteria. Heating is maintained for a time sufficient (as empirically determined) to reduce bacteria numbers. In one embodiment, a five-minute heating time is chosen. Sodium hexametaphosphate is then added as another antimicrobial agent. However, less sodium hexametaphosphate is needed inasmuch as a lower bacteria load exists in heated liquor compared to unheated liquor. Sodium hexametaphosphate acts as an antimicrobial by binding to the outer membrane of gram-negative bacteria, thereby facilitating the break down of the outer membrane. Target bacteria genuses include, but are not limited to *Pseudomonas, Escherichia,* and *Listeria*. Within those genuses, target species include *Pseudomonas aeruginosia, Escherichia coli,* and *Listeria monocytogenes.*

It is the temperature in combination with the time that is most critical to breaking down the outer membrane of the bacteria. The liquor is heated at the point of addition of the sodium hexametaphosphate. With some bacteria the outer membrane is broken down in seconds. The 5 minute minimum is based upon a non-linear pasteurization curve. That curve starts at 62.7 C for 30 minutes and goes through 84.4 C for 5 seconds. 70 C is more than twice the recommended time for the temperature, however the heat also provides a means for facilitating quick dissolution of the sodium hexametaphosphate.

Sodium hexametaphosphate also serves as a chelating agent. Sodium Hexametaphosphate is available at a myriad of commercial outlets, including Alfa Aesar of New York, N.Y.

Surprisingly and unexpectedly, the inventor found that heating the liquor containing both the sodium benzoate and the sodium hexametaphosphate cured the discoloration problem. The flavor stayed pure for 90 days in the lab. The sodium hexametaphosphate is especially useful to tie up the free minerals such as sulfur, which otherwise would be converted by sulfur degrading bacteria to foul smelling and tasting sulfur dioxide. Empirically, the amount of free ions is calculated in the mineral water supply, and a concentration of sodium hexametaphosphate determined to tie up the ions.

After suitable reaction with the sodium hexametaphosphate, a sequestration agent is added. Suitable sequestration agents include, but are not limited to EDTA, CarboxylMethyl Cellulose, and combinations thereof.

One of the salient features of the invention was ionic (i.e., noncovalent) sequestration of free minerals with EDTA. EDTA binds to multivalent ions via four carboxylate groups and two amine groups. It is especially important in the removal of Iron III, which would otherwise yellow the water when acted upon by iron degrading bacteria. Also, as these bacteria oxidize the iron, an off flavor results.

In sequestering the free minerals, EDTA also lowers the water activity. Initial tests by the inventor show a water activity level of 0.89 to 0.95. (Water activity is measured in the industry on a scale of 0 to 1.). Surprisingly and unexpectedly, after sterilizing the water with the addition of EDTA, water activity levels dropped to less than 0.75. This makes the invented food thickener less susceptible to *E. coli, Clostridium perfringens, Salmonella, C. botulinum, lactobacillus* and many yeasts and molds, thereby providing the heretofore discussed 150 day shelf life for air-exposed formulations.

An embodiment of the food thickener exhibits water activity levels of 0.67.

The inventor found that reducing the a.w. greater increased shelf life. Shelf lives of at least 120 days, and typically 150 days in sterile packaging are achieved when commercial packaging protocols are utilized. For example, "Bag-in-Box" liquid packaging is now common protocol in the packaging industry, with food packaged/bagged through a commercial Liquid Box bagger, such as Model 1000-cit-w from Liquibox Corporation, Akron, Ohio, as one example. Other liquid bag-in-box protocols will work as well. Preferably, shelf life is enhanced with the utilization of an inert fluid purge (i.e. nitrogen, helium, argon) at the beginning and end of bag fill cycles.

Protocol Detail

One embodiment of the invented process includes the following protocol: First, water used in the liquor must have particular characteristics. Suitable water is mineral water. Mineral water by definition has a Total Dissolved Solids (TDS) count of at least 280 mg/liter.

Mineral water with a pH of between 6.5 and 10 is suitable, with a pH of 8 preferable. The water is then filtered (activated carbon is a suitable filtration means) to remove free iron. The first filtered water is then subjected to subsequent filtration down to one micron (for example with the aid of a polywoven Rosedale screen) to further remove residual iron remaining from the carbon filtration step.

Optionally, the water is then subjected to UV radiation to eradicate any remaining viable microorganisms and fauna. If the water is known to not contain bromide, then ozonation can be utilized instead, or in conjunction with UV treatment.

In one embodiment, starting with mineral water, pH 8, 280 mg/l mineral content, the water is heated. After holding temperature for at least 5 minutes, sodium hexametaphosphate is added at a rate of 750 parts per million (ppm). Then, the liquor is heated to boiling for total dissolution and sterilization. About 35-40 ppm, and preferably 38 ppm EDTA is added and heated to <180 F. EDTA is required to sequester and otherwise isolate ions and free elements found in mineral water, namely calcium, iron, sulfur, phosphorus, bromides and magnesium.

Finally, clarified and hydrolyzed xanthan is added to the desired viscosity. The xanthan must be clarified for best results, as it will yellow if it is not clarified. Clarification before addition eliminates the need for filtering finished product for clarity.

A detailed protocol for another embodiment of the invention appears below:

1. Sodium benzoate—no greater than 0.05% by weight of finished product per FDA regulations. In the laboratory, a one liter flask is weighed, then filled exactly to one liter, and weighed again, so as to arrive at a grams per liter value. Then, 0.05 percent of the weight is determined by multiplying 0.0005 times the weight in grams. The sodium benzoate is added to water at room temperature. This is the first ingredient, added to the water at a rate of 5 minutes/100 gal water. Addition of sodium benzoate is done at room temperature. It is added first to slow or stop microbial action that may be occurring. It also aids in extending shelf life.

2. Sodium Hex—at 280 mg/L mineral content of water, add at a rate of 750 ppm, at approximately 77° C. Suitable temperatures range from 70° C. to less than 100° C. Preferably, the sodium hexametaphosphate is added after the water reaches 70° C. This type of flavor preserver is added at a rate of 3 minutes minimum/100 gal water.

3. EDTA—At 280 mg/L mineral content of water, add at a rate of 38 ppm at a temperature less than 100° C. so as to facilitate sequestration. Preferably, the EDTA is added at a temperature of approximately 77° C. Generally, as the liquor is heated from 77° C., more ions dissociate and make themselves available for sequestration.

The rate of addition of EDTA is 20 minutes, minimum. This ensures complete dissolution of all additives (i.e., a substantially homogeneous dispersion of the additive throughout the liquor). The 20 minute duration also is the minimum time necessary to kill any thermophillic bacteria/spores.

4. Xanthan (clarified and hydrolyzed for easy dispersal) is then added. The Xanthan is first clarified so as to achieve a powder color not less than 60. In one embodiment clarification (via high speed centrifugation, e.g., at from 1500 and 8000 rpms, usually at 2000 rpms or above, and preferably at 3600 rpms) occurs at room temperature.

The Xanthan is added at a preferable concentration of 31 grams/gal to achieve the aforementioned industry-specified viscosity values for "Honey" formulations. For "Nectar" viscosities, xanthan is added at a concentration of 24 grams/gal.

Xanthan disperses best and most quickly at higher temperatures. It is heat stable. It is added at a temperature above 95° C. so as to not trap oxygen from liquor agitation. Otherwise, the oxygen will facilitate bacterial growth. Preferably the xanthan is added at below the boiling temperature of the liquor. Xanthan additions below 100° C. are suitable. Preferably, mixing of Xanthan in the building liquor occurs at 95° C. only after product is held at 100° C. for 7 minutes (to kill sulfur degrading bacteria and any spores as well as to aid in dropping out of free iron and sulfur ions).

5. CarboxyMethylCellulose—1.0% by weight for the "Honey" consistency. CMC is added at approximately 95° C.

Surprisingly and unexpectedly, the inventor found that mineral water yielded the best results for producing the food thickener. Tests using this same formula for tap water and distilled water yielded an after taste and a white precipitate. Also, there was opacity associated with the tap water. The mineral water remained clear and tasteless, as well as odorless.

Using the invented method, longer shelf life of the resulting food thickner is attained, with none of the odor and color problems associated with the prior art formulations. Natural flavor of food is maintained. Also, the aftertaste associated with xanthan is eliminated.

Surprisingly and unexpectedly, the inventor found that by starting with mineral water at a pH of 8 or higher, using EDTA as a sequestrant, and sodium hexametaphosphate as a chelating agent, thickened water is produced having no acid taste or after-taste. This is because the at least pH 8 feature provides enough hydroxyl ions to aid in flavor as well as to aid in the chelation and sequestration processes. The negative charge of the hydroxyl ions repel the negatively charged carboxylate and amine groups of the EDTA. This allows the EDTA moieties to seek out and sequester, chelate or otherwise isolate positively charged metal ions in the liquor.

The invented process is illustrated in FIG. 1 as numeral 10. A mineral water source 12 provides water which typically contains chlorine 14. (Municipalities add chlorine to water supplies inasmuch as the electronegative chlorine pulls iron and other target moieties out of suspension. If chlorine levels are low, for example in water sources not municipal in nature, then iron degrading bacteria feeds on the free iron in the tap water to generate iron oxides, thereby also causing water to yellow over time.)

The mixture is placed in a holding tank 16. Settling of the mixture within the holding tank 16 results in precipitation of any free iron. The iron-free mixture then contacts a carbon bed 18 with the adsorption characteristics of the carbon bed resulting in chlorine ions and other undesirable ions being extracted from the mixture.

The mixture 20 is then subjected to a Rosedale filter 22 (i.e., a woven mesh filter approximately 1 inch thick that traps sediment). Once sediment is removed, the mixture is treated with what is called a UV "filter" 24 which is not a mechanical filter but a means for imparting UV radiation to the liquor.

A 0.5 micron filter 26 or similar porosity filter is utilized to remove any pathogens killed by the UV treatment, and the filtrate 28 is passed to a holding tank 30 capable of being heated. Sodium benzoate 32 (at 0.05 percent by weight of the finished product), discussed supra, is added to the holding tank.

While residing in the tank, the mixture is maintained at or above 70 C. Sodium hexametaphosphate 34 is then added at 750 ppm after which the liquor is further heated. Disodium EDTA 36 is then added at a concentration of 38 ppm and at a temperature of 77 C. After which, the liquor is heated and maintained at 100 C for at least seven minutes, but typically between 7 minutes and 10 minutes to facilitate reaction within the holding tank 30. Reaction times of more than 20 minutes are not typically necessary.

The liquor is allowed to cool to 95 C and transferred to a jacketed stainless steel batch tank having a shear rate of less than 100/second at 22 C. To the vortex imparted to the liquor by the batch tank operation is added clarified hydrolyzed xanthan 40. Prior to addition to the liquor the xanthan is pretreated. First, the xanthan is prepared in situ by treatment with a clarifier 42 whereby the clarifier (i.e., high speed centrifugation) spins at 3600 rpm. Then, just prior to addition to the liquor, carboxy methyl cellulose is added to the xanthan (whereby the cellulose is added to the clarified xanthan at a concentration of more than 1 percent weight of the finished product.

Upon addition of the xanthan to the liquor in the batch tank 38, the liquor is processed for at least 45 minutes or for a time sufficient to homogenize the constituents of the liquor. The liquor is then transferred to an APV Crepeco High Temperature, Short Time Pasteurizer and maintained at 180 F (82.22 C) for 27 seconds. Through-put of this APV unit 44 is 600 gph.

After processing with the APV unit 44, the liquor is transferred to an aseptic pressure vessel to facilitate packing into individual drink/food portions.

Alcoholic Beverage
Preparation Detail

Ethanol-containing beverages are just as sought after among patients with swallowing disorders as with persons not so disabled. A salient feature of the invented protocol is the filtration of spores from wine prior to mixture of the wine with xanthan-based food thickener.

Specifically, to enable wine drinkers suffering from dysphagia to again drink wine or beer, the following protocol is utilized:

Wine is treated for active yeast and spores by the addition of sulfites, potassium sorbate, sodium benzoate, u.v. radiation or filtration at values of no more than 6 microns (1 micron is preferred).

Once viable yeast/spores have been eradicated, the resulting ethanol-containing liquor is agitated and heated to no more than 100° C. (with 37° C. being preferred). EDTA is added at a rate of 5-50 ppm, with a preferred inclusion rate of 38 ppm. This will ultimately be determined empirically, depending on the palate of the market and the beverage (wine or beer) being modified.

Clarified xanthan is then added at a rate of 3-8 g/L for Nectar-consistency beverages (such as lighter body wines and beer), and greater than 8 g/L for Honey-consistency beverages. Wine should be agitated until clear, bottled and cooled to room temperature or below. Generally, the fewer the spores remaining after filtration the better. The inventor found that less than 100 spores per liter after treatment yielded acceptable taste characteristics, and preferably less than 50 spores.

Swallow Inducing
Protocol Detail

As noted supra, the invention enables a method for inducing the swallow reflex in patients who have lose sensitivity in portions of their tongue and mouths. Surprisingly and unexpectedly, the inventor found that density of fluid placed on the tongue of these patients is more important than viscosity, of the fluid. Empirical data reveals that when food (or water) is thickened with the invented thickener to a mass of between 750 and 1250 grams/liter, and preferably to about 1000 grams per liter, a swallowing response is induced. Therefore, such densities provide a means for inducing swallowing in patients with dysphagia.

The swallowing-inducing method comprises mixing a quantity of food thickener with nourishment to create a mixture, wherein the resulting mixture has a density of about 1000 g/liter; and orally administering the mixture to a person suffering from dysphagia. The inventor found that when the thickener-food mixture contacts portions of a patient's tongue, usually the rearward portion of the top surface of the tongue, the gravity induced pressure of the mixture against the tongue induces the patient to swallow the mixture. Generally, the weight percent of the invented thickener product to the entire weight of the mixture is at least 1.3 percent, and preferably between 1.35 percent and 1.8 percent.

In summary, the invention provides a food thickening agent which is produced at and maintained at neutral to alkaline pH levels. A characteristic of the thickening agent is its ability to minimize water activity levels, when a preferred embodiment of the thickener is utilized.

Preservation of the thickener occurs with sterilization using a myriad of commercially available means, including but not limited to high temperature treatment (to a maximum of 110° C. for 2 hours), ultra violet treatment (between 200 and 280 nm and preferably 254 nm), ultra filtration (ranging between 0.01 microns and 2 microns, and preferably 0.05 microns) or irradiation (alpha, beta or gamma radiation).

While the invention has been described with reference to details of the illustrated embodiment, these details are not intended to limit the scope of the invention as defined in the appended claims. For example, the use of the invented food thickener in baby formula facilitates hydration of the infant without the need for added chemicals, otherwise necessary to keep down microbial growth.

Another embodiment of the food thickener is as constituent in sports drinks. In this embodiment a reduced inclusion rate (i.e., reduced concentration) of the xanthan is utilized, along with a concomitant increased concentration of isotonic electrolytes and flavors. The xanthan-containing sports drink provides a means for keeping the throat moist longer than if water only was used. Alternatively, instead of providing a hydrated thickener for use in sports drinks, a dry mixture of the thickener is provided, sans mineral water. In this way, the end user mixes tap water with the dry mixture before ingesting the thickened exercise drink. In either the hydrated or dried version, the inventor found that athletes utilizing the mixture found it as a means to control swallowing while running, which is of particular interest to marathon runners and extreme-sports enthusiasts.

The embodiment of the invention in which an exclusive property or privilege is claimed is defined as follows:

1. A method for preparing food and liquid thickener, the method comprising:
   a) pretreating mineral water;
   b) combining the pretreated mineral water with a food preservative to produce a first mixture, said food preservative comprising a salt of benzoic acid;
   c) heating the first mixture to a first temperature and then combining the heated mixture with a chelating agent to produce a second mixture, said chelating agent comprising sodium hexametaphosphate;
   d) combining the second mixture with a sequestering agent to form a third mixture and then maintaining the third mixture at a second temperature, said sequestering agent being present in an amount effective to lower water activity to below 0.75, said sequestering agent comprising EDTA; and
   e) adding a thickener selected from the group consisting of xanthan, Carrageenan, Guar Gum, carboxymethyl cellulose, modified food starch, and combinations thereof to the third mixture to create a fourth mixture.

2. The method as recited in claim 1 wherein the thickener is xanthan and wherein the xanthan is first clarified.

3. The method as recited in claim 1 wherein the food thickener is combined with nourishment to produce a liquor with a density of 1000 g/liter.

4. The method as recited in claim 3 wherein the liquor induces a swallowing reflex in dysphagic patients.

5. A method for producing alcoholic beverages, the method comprising:
   a) pretreating mineral water;
   b) combining the pretreated mineral water with a food preservative to produce a first mixture, said food preservative comprising a salt of benzoic acid;
   c) heating the first mixture to a first temperature and then combining the heated mixture with a chelating agent to produce a second mixture, said chelating agent comprising sodium hexametaphosphate;

d) combining the second mixture with a sequestering agent to form a third mixture and then maintaining the third mixture at a second temperature, said sequestering agent being present in an amount effective to lower water activity to below 0.75, said sequestering agent comprising EDTA;

e) adding a thickener selected from the group consisting of xanthan, Carrageenan, Guar Gum, carboxymethyl cellulose, modified food starch, and combinations thereof to the third mixture to create a fourth mixture;

f) optionally homogenizing the fourth mixture; and g) mixing the fourth mixture with fluid containing ethanol.

6. The method as recited in claim 5 wherein the fluid containing ethanol is pretreated to decrease the concentration of spores in the fluid to less than 50 per liter.

7. The method as recited in claim 5 wherein the fluid containing ethanol is a liquid selected from the group consisting of wine, beer, and distilled spirits.

8. The method as recited in claim 5 wherein the weight percent of fluid containing ethanol to the homogenized mixture is between 98.5 and 99.3 percent.

9. The method of claim 1, further compromising homogenizing the fourth mixture.

10. The method of claim 5, wherein the fourth mixture is homogenized.

11. A food and liquid thickener prepared in accordance with the method of claim 1.

12. A food and liquid thickener prepared by the method of claim 2.

13. An alcoholic beverage produced by the method of claim 9.

14. A method according to claim 1, said thickener comprising xanthan.

15. A method according to claim 3, said thickener comprising xanthan.

16. A method according to claim 4, said thickener comprising xanthan.

17. A method according to claim 5, said thickener comprising xanthan.

18. A method according to claim 6, said thickener comprising xanthan.

19. A method according to claim 7, said thickener comprising xanthan.

20. A method according to claim 8, said thickener comprising xanthan.

21. A method according to claim 9, said thickener comprising xanthan.

22. A method according to claim 10, said thickener comprising xanthan.

23. A food and liquid thickener according to claim 11, said thickener comprising xanthan.

24. A food and liquid thickener according to claim 12, said thickener comprising xanthan.

25. An alcoholic beverage according to claim 13, said thickener comprising xanthan.

26. A method for preparing food and liquid thickener, the method comprising:

a) pretreating mineral water;

b) combining the pretreated mineral water with a food preservative to produce a first mixture, said food preservative comprising a salt of benzoic acid;

c) heating the first mixture to a first temperature and then combining the heated mixture with a chelating agent to produce a second mixture, said chelating agent comprising sodium hexametaphosphate;

d) combining the second mixture with a sequestering agent to form a third mixture and then maintaining the third mixture at a second temperature, said sequestering agent being present in an amount of 10-30 mg/liter, said sequestering agent comprising EDTA; and e) adding a thickener selected from the group consisting of xanthan, Carrageenan, Guar Gum, carboxymethyl cellulose, modified food starch, and combinations thereof to the third mixture to create a fourth mixture.

27. The method as recited in claim 26 wherein the thickener is xanthan and wherein the xanthan is first clarified.

28. The method as recited in claim 26 wherein the food thickener is combined with nourishment to produce a liquor with a density of 1000 g/liter.

29. The method as recited in claim 28 wherein the liquor induces a swallowing reflex in dysphagic patients.

30. The method of claim 26, further compromising homogenizing the fourth mixture.

31. A food and liquid thickener prepared in accordance with the method of claim 26.

32. A food and liquid thickener prepared by the method of claim 27.

* * * * *